US006511839B1

(12) United States Patent
Chan et al.

(10) Patent No.: US 6,511,839 B1
(45) Date of Patent: Jan. 28, 2003

(54) FUCOSE KINASE

(76) Inventors: Pan Fong Chan, SmithKline Beecham Corporation, Corporate Intellectual Property - UW2220, P.O. Box 1539, King of Prussia, PA (US) 19406-0939; Sanjoy Biswas, SmithKline Beecham Corporation, Corporate Intellectual Property - UW2220, P.O. Box 1539, King of Prussia, PA (US) 19406-0939; David J. Holmes, SmithKline Beecham Corporation, Corporate Intellectual Property - UW2220, P.O. Box 1539, King of Prussia, PA (US) 19406-0939; Michael A. Lonetto, SmithKline Beecham Corporation, Corporate Intellectual Property - UW2220, P.O. Box 1539, King of Prussia, PA (US) 19406-0939; Leslie M. Palmer, SmithKline Beecham Corporation, Corporate Intellectual Property - UW2220, P.O. Box 1539, King of Prussia, PA (US) 19406-0939; Stephanie Van Horn, SmithKline Beecham Corporation, Corporate Intellectual Property - UW2220, P.O. Box 1539, King of Prussia, PA (US) 19406-0939; Richard L. Warren, Jr., SmithKline Beecham Corporation, Corporate Intellectual Property - UW2220, P.O. Box 1539, King of Prussia, PA (US) 19406-0939; Magdalena Zalacain, SmithKline Beecham Corporation, Coporate Intellectual Property - UW2220, P.O. Box 1539, King of Prussia, PA (US) 09406-0939

( * ) Notice: Subject to any disclaimer, the term of this patent is extended or adjusted under 35 U.S.C. 154(b) by 17 days.

(21) Appl. No.: 09/591,041

(22) Filed: Jun. 9, 2000

Related U.S. Application Data

(60) Provisional application No. 60/140,348, filed on Jun. 22, 1999.

(51) Int. Cl.[7] .......................... C12N 15/11; C12N 1/21; C12N 5/10; C12N 15/63

(52) U.S. Cl. ................. 435/252.3; 435/325; 435/320.1; 435/69.1; 536/24.1

(58) Field of Search ...................... 536/24.1; 435/320.1, 435/252.3, 69.1

(56) References Cited

PUBLICATIONS

Chen, et al., "The organization of the *fuc* regulon specifying L–fucose dissimilation in *Escherichia coli* K12 as determined by gene cloning", *Mol. Gen. Genet* (*1987*), vol. 210, pp. 331–337.

Chen, et al., "Cross–Induction of the L–Fucose System by L–Rhamnose in *Escherichia coli", Journal of Bacteriology*, Aug. 1987, vol. 169, No. 8, pp. 3712–3719.

*Primary Examiner*—Rebecca E. Prouty

(57) ABSTRACT

The invention provides fucose kinase promoter polynucleotides and methods for producing and using such polynucleotides, as well as their variants, agonists and antagonists, and their uses.

3 Claims, No Drawings

SEQUENCE LISTING

```
<160> NUMBER OF SEQ ID NOS: 5

<210> SEQ ID NO 1
<211> LENGTH: 181
<212> TYPE: DNA
<213> ORGANISM: Streptococcus pneumoniae

<400> SEQUENCE: 1

cataagctcc tcctaattta tcatttcaac tatattatag cacaaattgg aggaatttga     60

attattttta tgaatattgg gttaacattt gaacattatc caagtaagcg ttcacatatt    120

gaaaaaataa aatgtgggga ttataataaa cttaatcaag gacgaagaga gaagaaaaat    180

g                                                                    181


<210> SEQ ID NO 2
<211> LENGTH: 11
<212> TYPE: DNA
<213> ORGANISM: Streptococcus pneumoniae
<220> FEATURE:
<221> NAME/KEY: misc_feature
<222> LOCATION: (1)...(11)
<223> OTHER INFORMATION: n = A,T,C or G

<400> SEQUENCE: 2

tntgntataa t                                                          11


<210> SEQ ID NO 3
<211> LENGTH: 31
<212> TYPE: DNA
<213> ORGANISM: Streptococcus pneumoniae

<400> SEQUENCE: 3

caagaatttt agctagtaga aagtcaatat c                                    31


<210> SEQ ID NO 4
<211> LENGTH: 19
<212> TYPE: DNA
<213> ORGANISM: streptococcus pneumoniae

<400> SEQUENCE: 4
```

-continued

```
atccgcttgg ctaatacta                                                   19


<210> SEQ ID NO 5
<211> LENGTH: 19
<212> TYPE: DNA
<213> ORGANISM: streptococcus pneumoniae

<400> SEQUENCE: 5

atcgcctaaa ccatactcc                                                   19
```

FUCOSE KINASE

RELATED APPLICATION

This application claims benefit to U.S. Provisional Patent Application No. 60/140,348 filed Jun. 22, 1999

FIELD OF THE INVENTION

This invention relates to newly identified polynucleotides, and their production and uses, as well as their variants, agonists and antagonists, and their uses. In particular, the invention relates to promoter polynucleotides, as well as their variants, hereinafter referred to as "fucose kinase," "fucose kinase promoter polynucleotide(s)," and "fucose kinase polynucleotide(s)" as the case may be.

BACKGROUND OF THE INVENTION

The Streptococci make up a medically important genera of microbes known to cause several types of disease in humans, including, for example, otitis media, conjunctivitis, pneumonia, bacteremia, meningitis, sinusitis, pleural empyema and endocarditis, and most particularly meningitis, such as for example infection of cerebrospinal fluid. Since its isolation more than 100 years ago, *Streptococcus pneumoniae* has been one of the more intensively studied microbes. For example, much of our early understanding that DNA is, in fact, the genetic material was predicated on the work of Griffith and of Avery, Macleod and McCarty using this microbe. Despite the vast amount of research with *S. pneumoniae*, many questions concerning the virulence of this microbe remain. It is particularly preferred to employ Streptococcal genes and gene products as targets for the development of antibiotics.

The frequency of *Streptococcus pneumoniae* infections has risen dramatically in the past few decades. This has been attributed to the emergence of multiply antibiotic resistant strains and an increasing population of people with weakened immune systems. It is no longer uncommon to isolate *Streptococcus pneumoniae* strains that are resistant to some or all of the standard antibiotics. This phenomenon has created an unmet medical need and demand for new antimicrobial agents, vaccines, drug screening methods, and diagnostic tests for this organism.

Moreover, the drug discovery process is currently undergoing a fundamental revolution as it embraces "functional genomics," that is, high throughput genome- or gene-based biology. This approach is rapidly superseding earlier approaches based on "positional cloning" and other methods. Functional genomics relies heavily on the various tools of bioinformatics to identify gene sequences of potential interest from the many molecular biology databases now available as well as from other sources. There is a continuing and significant need to identify and characterize further genes and other polynucleotides sequences and their related polypeptides, as targets for drug discovery.

Clearly, there exists a need for polynucleotides, such as the fucose kinase polynucleotide embodiments of the invention, that have a present benefit of, among other things, being useful to screen compounds for antimicrobial activity. Such factors are also useful to determine their role in gene regulation, pathogenesis of infection, dysfunction and disease. There is also a need for identification and characterization of such factors and their antagonists and agonists to find ways to prevent, ameliorate or correct such infection, dysfunction and disease.

SUMMARY OF THE INVENTION

The present invention relates to fucose kinase, in particular fucose kinase promoter polynucleotides, recombinant materials and methods for their production. In another aspect, the invention relates to methods for using such polynucleotides, including treatment of microbial diseases, amongst others. In a further aspect, the invention relates to methods for identifying agonists and antagonists using the materials provided by the invention, and for treating microbial infections and conditions associated with such infections with the identified agonist or antagonist compounds. In a still further aspect, the invention relates to diagnostic assays for detecting diseases associated with microbial infections and conditions associated with such infections, such as assays for detecting fucose kinase promoter driven expression or activity.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to fucose kinase polynucleotides as described in greater detail below. In particular, the invention relates to polynucleotides of a fucose kinase of *Streptococcus pneumoniae*, which is related by sequence homology to no homolog polynucleotide or by the presence of characteristic motifs. The invention relates especially to fucose kinase promoter polynucleotides having the nucleotides sequences set out in Table 1. Note that sequences recited in the Sequence Listing below as "DNA" represent an exemplification of the invention, since those of ordinary skill will recognize that such sequences can be usefully employed in polynucleotides in general, including ribopolynucleotides.

TABLE 1

| fucose kinase Polynucleotide Promoter Sequences |
|---|
| (A) *Streptococcus pneumoniae* fucose kinase polynucleotide sequence [SEQ ID No:1].<br>5'-<br>CATAAGCTCCTCCTAATTTATCATTTCAACTATATTATAGCACAAATTGGAGGAATTTGAATTATTTTTATGAA<br>TATTGGGTTAACATTTGAACATTATCCAAGTAAGCGTTCACATATTGAAAAAATAAAATGTGGGGATTATAATA<br>AACTTAATCAAGGACGAAGAGAGAAGAAAATG-3' |

Methods to identify promoters include techniques known in the art as well as those provided herein. Art techniques include, but are not limited to, the following.

RT-PCR

RT-PCR analysis of total RNA isolated from infected tissue or in vitro grown cells. Using genome databases, primer pairs are designed to predict transcripts of the selected pathogen and arrayed in microtiter dish format. Total RNA is isolated from an in vitro grown pathogen and RT-PCR performed with all the primer pairs. Similarly RT-PCR is performed with total RNA isolated at varying times from infections of the selected pathogen in a variety of appropriate animal models. Comparison of the PCR profiles which reflect the ratio of a given mRNA to internal standards such as rRNA or housekeeping genes provides identification of those transcripts which are essentially absent in vitro, but are on throughout, or during, various phases of infection.

Putative promoters are characterized using TaqMan quantitative RT-PCR, or expression of reporter genes.

Specific sequence detection occurs by amplification of target sequences in the PE Applied Biosystems 7700 Sequence Detection System in the presence of an oligonucleotide probe labeled at the 5' and 3' ends with a reporter and quencher fluorescent dye, respectively (TaqMan FQ probe), which anneals between the two PCR primers. Only specific product will be detected when the probe is bound between the primers. As PCR amplification proceeds, the 5'-nuclease activity of Taq polymerase initially cleaves the reporter dye from the probe. The signal generated when the reporter dye is physically separated from the quencher dye is measured with an attached CCD camera. Each signal generated equals one probe cleaved which corresponds to amplification of one target strand.

RT/PCR controls may include +/−reverse transcriptase reactions, amplification along side genes known to be transcribed under the conditions of study and amplification of serial dilutions of genomic DNA. The level of transcription under in vivo and in vitro conditions is quantified by comparison of signal generated from these samples to that of a standard curve generated from signal resulting from amplification of the genomic DNA.

FAM and TAMRA labeling of primers and the uses of such primers has been reported. (Lee, L G, Connell, C R, and Bloch, W. 1993. Allelic discrimination by nick-translation PCR with fluorogenic probes. Nucleic Acids Research 21:3761–3766; Livak, K J, Flood, S J A, Marmaro, J., Giusti, W. and Deetz, K. 1995. Oligonucleotides with fluorescent dyes at opposite ends provide a quenched probe system useful for detecting PCR product and nucleic acid hybridization. PCR Methods and Applications 4:357–362.)

And/or the promoter region can be cloned upstream of a reporter gene in a vector appropriate for the selected pathogen. By "appropriate" it is meant a vector capable of replicating stably in a selected pathogen.

Potential reporter genes include, but are not limited to, beta-galactosidase, beta-lactamase, bacterial luciferase, firefly luciferase, beta-glucuronidase. Many other reporter genes known in the art may be used in the methods and compositions of matter of the invention.

Primer Extension

A primer especific for the gene which transcription to be analyse is designed at the appropiate distance from the ATG start codon. Total RNA is isolated from an in vitro grown pathogen and a reverse transcriptase reaction is carried out. Primers are fluorescently labelled at the 5' end using FAM, HEX or NED dyes. Primer extension products can be separated on a polyacrylamide sequencing gel and detected using a suitable gel scanning system (e.g. ABI Prism™ 377 Sequencer using GeneScan™ software as supplied by Perkin Elmer).

Deposited Materials

A deposit containing a *Streptococcus pneumoniae* 0100993 strain has been deposited with the National Collections of Industrial and Marine Bacteria Ltd. (herein "NCIMB"), 23 St. Machar Drive, Aberdeen AB2 1RY, Scotland on Apr. 11, 1996 and assigned deposit number 40794. The deposit was described as *Streptococcus pneumoniae* 0100993 on deposit.

On Apr. 17, 1996 a *Streptococcus pneumoniae* 0100993 DNA library in *E. coli* was similarly deposited with the NCIMB and assigned deposit number 40800. The *Streptococcus pneumoniae* strain deposit is referred to herein as "the deposited strain" or as "the DNA of the deposited strain."

The deposited strain contains the fill length fucose kinase gene comprising the promoter polynucleotide of the invention. The sequence of the promoter polynucleotides contained in the deposited strain, are controlling in the event of any conflict with any description of sequences herein.

The deposit of the deposited strain has been made under the terms of the Budapest Treaty on the International Recognition of the Deposit of Micro-organisms for Purposes of Patent Procedure. The deposited strain will be irrevocably and without restriction or condition released to the public upon the issuance of a patent. The deposited strain is provided merely as convenience to those of skill in the art and is not an admission that a deposit is required for enablement, such as that required under 35 U.S.C. §112. A license may be required to make, use or sell the deposited strain, and compounds derived therefrom, and no such license is hereby granted.

In one aspect of the invention there is provided an isolated nucleic acid molecule functional in the *Streptococcus pneumoniae* 0100993 strain, which polynucleotide is contained in the deposited strain. Further provided by the invention are fucose kinase polynucleotide sequences in the deposited strain, such as DNA and RNA, and amino acid sequences encoded thereby. Also provided by the invention are fucose kinase polynucleotide sequences isolated from the deposited strain.

Polynucleotides

It is an object of the invention to provide promoter polynucleotides from a fucose kinase gene. In a particularly preferred embodiment of the invention the polynucleotide comprises a promoter region from fucose kinase gene comprising a sequence set out in Table 1 [SEQ ID NO:1], or a variant thereof.

As a further aspect of the invention there are provided isolated promoter nucleic acid molecules from a fucose kinase gene, including, for example, polynucleotides derived from such molecules, such as, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides, and variants thereof, and compositions comprising the same.

Another aspect of the invention relates to isolated polynucleotides, including, for example polynucleotides closely related to a fucose kinase promoter having a polynucleotide sequence of Table 1 [SEQ ID NO:1].

In another particularly preferred embodiment of the invention there is a fucose kinase polynucleotide from *Streptococcus pneumoniae* comprising or consisting of an nucleotide sequence of Table 1 [SEQ ID NO:1], or a variant thereof.

Using the information provided herein, such as a promoter polynucleotide sequence set out in Table 1 [SEQ ID NO:1], a polynucleotide of the invention may be obtained using standard cloning and screening methods, such as those for cloning and sequencing chromosomal (genomic) DNA fragments from bacteria using *Streptococcus pneumoniae* 0100993 cells as starting material, followed by obtaining a related or equivalent sequence. For example, to obtain a polynucleotide sequence of the invention, such as a polynucleotide sequence given in Table 1 [SEQ ID NO:1], typically a library of clones of chromosomal DNA of *Streptococcus pneumoniae* 0100993 in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polynucleotide sequence it is then possible to extend the polynucleotide sequence in both directions to determine a functional promoter region sequence or full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA. sequencing may also be performed to obtain a promoter sequence of expressibly linked full length gene sequence. Illustrative of the invention, each polynucleotide set out in Table 1 [SEQ ID NO:1] was discovered in a DNA library derived from *Streptococcus pneumoniae* 0100993.

In a further aspect, the present invention provides for an isolated polynucleotide comprising or consisting of a polynucleotide sequence which has at least 70% identity, preferably at least 80% identity, more preferably at least 90% identity, yet more preferably at least 95% identity, even more preferably at least 97–99% or exact identity, to SEQ ID NO:1 over the entire length of SEQ ID NO:1.

A polynucleotide encoding a polypeptide of the present invention, including homologs and orthologs from species other than *Streptococcus pneumoniae*, may be obtained by a process which comprises the steps of screening an appropriate library under stringent hybridization conditions with a labeled or detectable probe consisting of or comprising the sequence of SEQ ID NO:1 or a fragment thereof, and isolating a promoter and/or full-length gene and/or genomic clones containing said polynucleotide sequence.

The invention also includes a polynucleotide consisting of or comprising a polynucleotide of the formula:

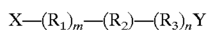

$$X—(R_1)_m—(R_2)—(R_3)_nY$$

wherein, at the 5' end of the molecule, X is hydrogen, a metal or a modified nucleotide residue, or together with Y defines a covalent bond, and at the 3' end of the molecule, Y is hydrogen, a metal, or a modified nucleotide residue, or together with X defines the covalent bond, each occurrence of $R_1$ and $R_3$ is independently any nucleic acid residue or modified nucleic acid residue, m is an integer between 1 and 3000 or zero , n is an integer between 1 and 3000 or zero, and $R_2$ is a nucleic acid sequence or modified nucleic acid sequence of the invention, particularly a nucleic acid sequence selected from Table 1 or a modified nucleic acid sequence thereof In the polynucleotide formula above, $R_2$ is oriented so that its 5' end nucleic acid residue is at the left, bound to $R_1$, and its 3' end nucleic acid residue is at the right, bound to $R_3$. Any stretch of nucleic acid residues denoted by either $R_1$ and/or $R_2$, where m and/or n is greater than 1, may be either a heteropolymer or a homopolymer, preferably a heteropolymer. Where, in a preferred embodiment, X and Y together define a covalent bond, the polynucleotide of the above formula is a closed, circular polynucleotide, which can be a double-stranded polynucleotide wherein the formula shows a first strand to which the second strand is complementary. In another preferred embodiment m and/or n is an integer between 1 and 1000. Other preferred embodiments of the invention are provided where m is an integer between 1 and 50, 100 or 500, and n is an integer between 1 and 50, 100, or 500.

It is most preferred that a polynucleotide of the invention is derived from *Streptococcus pneumoniae*, however, it may preferably be obtained from other organisms of the same taxonomic genus. A polynucleotide of the invention may also be obtained, for example, from organisms of the same taxonomic family or order.

Preferred embodiments are polynucleotides that retain substantially the same biological function or activity as the promoter region DNA of Table 1 [SEQ ID NO:1].

In accordance with certain preferred embodiments of this invention there are provided polynucleotides that hybridize, particularly under stringent conditions, to fucose kinase polynucleotide sequences, such as those polynucleotides in Table 1. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml of denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention. Preferred polynucleotides that hybridize under stringent conditions are polynucleotide sequences comprising of at least 50, 100, 500, 1000, or 3000 nucleotides.

As discussed elsewhere herein regarding polynucleotide assays of the invention, for instance, the polynucleotides of the invention, may be used as a hybridization probe genomic DNA to isolate genomic clones encoding fucose kinase and to isolate genomic clones of other genes that have a high identity, particularly high sequence identity, to the fucose kinase gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have lee than 30 nucleotide residues or base pairs.

The polynucleotides of the invention may be employed, for example, as research reagents and materials for discovery of treatments of and diagnostics for diseases, particularly human diseases, as further discussed herein relating to polynucleotide assays.

For each and every polynucleotide of the invention there is provided a polynucleotide complementary to it. It is preferred that these complementary polynucleotides are fully complementary to each polynucleotide with which they are complementary.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

Vectors, Host Cells, Expression Systems

The invention also relates to vectors that comprise a polynucleotide or polynucleotides of the invention, host cells that are genetically engineered with vectors of the invention and the production of polynucleotides of the invention by recombinant techniques. Further the promoter polynucleotides of the invention can be used to drive the expression of heterologous proteins or over-expression of naturally associated proteins. Since the promoter polynucleotide of the invention is inducible, such as by mannose or by any other appropriate inducers as the case may be, in other aspect the further aspect relates to direct or indirect up- or down-regulation of expression or transcription of a target gene. Recombinant proteins (polypeptides) may be prepared by processes well known in the art from genetically engineered host cells comprising expression vectors.

For recombinant production of the polynucleotides of the invention, host cells can be genetically engineered to incorporate replication systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL,* 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection. Representative examples of appropriate hosts include bacterial cells, such as cells of streptococci, staphylococci, enterococci, *E. coli*, streptomyces, cyanobacteria, *Bacillus subtilis*, and *Streptococcus pneumoniae*; fungal cells, such as cells of a yeast, Kluveromyces, Saccharomyces, a basidiomycete, *Candida albicans* and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of replication systems can be used to produce the polynucleotides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picornaviruses and retroviruses, and vectors derived from combinations thereof, such as those derived from plasmid and bacteriophage genetic elements, such as cosmids and phagemids. The replication system constructs may contain control regions other than the promoter of the invention that regulate as well as engender expression, such as marker gene expression. Generally, any system or vector suitable to maintain, propagate or express polynucleotides in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL* , (supra).

Assays, Antagonists and Agonists

Characterization of Function

Assays of the invention may be performed by determining the effect of transcript level on cell phenotype. These assays will help to characterize, among other things, temporal relevance of transcription to phenotype.

Protein Expression

Promoter polynucleotides of the invention may be used for overproduction of heterologous proteins in bacteria.

Essentiality Testing

Promoter polynucleotides of the invention may be used to assess gene essentiality in a bacteria. Example 2 provides one embodiment of this type of assay. Skilled artisans can readily determine other ways to perform such analyses based on the present invention and the teachings herein.

Polynucleotides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al, *Current Protocols in Immunology* 1(2): Chapter 5 (1991).

Polynucleotides of the present invention are responsible for many biological functions, including many disease states, in particular the Diseases hereinbefore mentioned. It is therefore desirable to devise screening methods to identify compounds which stimulate or which inhibit the function of the polynucleotide. Accordingly, in a further aspect, the present invention provides for a method of screening compounds to identify those which stimulate or which inhibit the function of a polynucleotide of the invention, as well as related polynucleotides. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of fucose kinase polynucleotides; or may be structural or functional mimetics thereof (see Coligan et al, *Current Protocols in Immunology* 1(2): Chapter 5 (1991)).

The screening methods may simply measure the binding of a candidate compound to the polynucleotide, or to cells or membranes bearing the polynucleotide. Alternatively, the screening method may involve competition with a labeled competitor. Further, these screening methods may test whether the candidate compound results in a signal generated by activation or inhibition of the polynucleotide, using detection systems appropriate to the cells comprising the polynucleotide. Inhibitors of activation are generally assayed in the presence of a known agonist and the effect on activation by the agonist by the presence of the candidate compound is observed. Constitutively active promoter polynucleotides and/or constitutively expressed polynucleotides may be employed in screening methods for inverse agonists or inhibitors, in the absence of an agonist or inhibitor, by testing whether the candidate compound results in inhibition of activation of the polynucleotide, as the case may be. Further, the screening methods may simply comprise the steps of mixing a candidate compound with a solution containing a polynucleotide of the present invention, to form a mixture, measuring fucose kinase promoter polynucleotide activity in the mixture, and comparing the fucose kinase promoter polynucleotide activity of the mixture to a standard. Fusion proteins, such as those made from $F_c$ portion and fucose kinase promoter polynucleotide, as hereinbefore described, can also be used for high-throughput screening assays to identify antagonists of the polynucleotide of the present invention, as well as of phylogenetically and and/or functionally related promoters.

The polynucleotides, polypeptides and antibodies that bind to and/or interact with a polynucleotide of the present invention may also be used to configure screening methods for detecting the effect of added compounds on the production of mRNA and/or promoter polynucleotide in cells.

The invention also provides a method of screening compounds to identify those which enhance (agonist) or block (antagonist) the action of fucose kinase polynucleotides, particularly those compounds that are bacteristatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising fucose kinase polynucleotide and a labeled substrate or ligand of such polynucleotide is incubated in the absence or the presence of a candidate molecule that may be a fucose kinase agonist or antagonist. The ability of the candidate molecule to agonize or antagonize the fucose kinase polynucleotide is reflected in decreased binding of the labeled ligand or decreased production of product from such substrate. Molecules that bind gratuitously, i.e., without inducing the effects of fucose kinase polynucleotide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in fucose kinase polynucleotide activity, and binding assays known in the art.

Polynucleotides of the invention may be used to identify promoter binding proteins, such as sigma factors, if any, for such polynucleotide, through standard binding techniques known in the art, for example, gel retardation assays. Other of these techniques include, but are not limited to, ligand binding and crosslinking assays in which the polynucleotide is labeled with a radioactive isotope (for instance, $^{32}P$), chemically modified (for instance, biotinylated or fluorescent tagged), or fused to a polynucleotide sequence suitable for detection or purification, and incubated with a source of the putative binding compound or ligand (e.g., cells, cell membranes, cell supernatants, tissue extracts, bodily materials). Other methods include biophysical techniques such as surface plasmon resonance and spectroscopy. These screening methods may also be used to identify agonists and antagonists of the polynucleotide which compete with the binding of the polynucleotide to its ligand(s), if any. Standard methods for conducting such assays are well understood in the art.

The fluorescence polarization value for a fluorescently-tagged molecule depends on the rotational correlation time or tumbling rate. Protein-polynucleotide complexes, such as formed by fucose kinase polynucleotide associating with polypeptide or other factor, labeled to comprise a fluorescently-labeled molecule will have higher polarization values than a fluorescently labeled monomeric polynucleotide. It is preferred that this method be used to characterize small molecules that disrupt polypeptide-polynucleotide complexes.

Fluorescence energy transfer may also be used to characterize small molecules that interfere with the formation of fucose kinase polynucleotide-polypeptide dimers, trimers, tetramers or higher order structures, or structures formed by fucose kinase polynucleotide and a polypeptide or polypeptides. Fucose kinase polynucleotides can be labeled with both a donor and acceptor fluorophore. Upon mixing of the two labeled species and excitation of the donor fluorophore, fluorescence energy transfer can be detected by observing fluorescence of the acceptor. Compounds that block dimerization will inhibit fluorescence energy transfer.

In other embodiments of the invention there are provided methods for identifying compounds which bind to or otherwise interact with and inhibit or activate an activity or expression of a polynucleotide of the invention comprising: contacting a polynucleotide of the invention with a compound to be screened under conditions to permit binding to or other interaction between the compound and the polynucleotide to assess the binding to or other interaction with the compound, such binding or interaction preferably being associated with a second component capable of providing a detectable signal in response to the binding or interaction of the polynucleotide with the compound; and determining whether the compound binds to or otherwise interacts with and activates or inhibits an activity or expression of the polynucleotide by detecting the presence or absence of a signal generated from the binding or interaction of the compound with the polynucleotide.

Another example of an assay for fucose kinase agonists or antagonists is a competitive assay that combines fucose kinase and a potential agonist or antagonist with fucose kinase-binding molecules, recombinant fucose kinase binding molecules, natural substrates or ligands, or substrate or ligand mimetics, under appropriate conditions for a competitve inhibition assay. Fucose kinase can be labeled, such as by radioactivity or a colorimetric compound, such that the number of fucose kinase molecules bound to a binding molecule or converted to product can be determined accurately to assess the effectiveness of the potential antagonist or agonist.

Numerous assays may be used with the preferred inducible promoters of the invention, as provided herein an as known in the art. These assays include, but are not limited to the following.

Antimicrobial Compound Testing

Promoter polynucleotides of the invention may also be used to determine a target of unknown antibacterial susceptibility.

Promoter polynucleotides of the invention may also be used to assess the effect of transcript level on antibacterial susceptibility.

Still further, promoter polynucleotides of the invention may also be used in whole cell screens.

Inducible promoters can be used to up and down regulate expression of target gene directly, or indirectly by transcription anti-sense RNA or ribozymes.

Potential antagonists include, among others, small organic molecules, peptides, polypeptides that bind to a polynucleotide of the invention and thereby inhibit or extinguish its activity or expression. Potential antagonists also may be small organic molecules, a peptide, a polypeptide such as a closely related protein that binds the same sites on a binding molecule, such as a binding molecule, without inducing fucose kinase promoter-induced activities, thereby preventing the action of fucose kinase polynucleotides by excluding fucose kinase polynucleotides from binding.

Potential antagonists include a small molecule that binds to and occupies the binding site of the polynucleotide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXY-NUCLEOTIDES AS ANTISENSE INHIBITORS OF GENE EXPRESSION*, CRC Press, Boca Raton, Fla. (1988), for a description of these molecules). Preferred potential antagonists include compounds related to and variants of fucose kinase.

Other examples of potential polypeptide antagonists include oligonucleotides or proteins which are closely related to the ligands, substrates, receptors, enzymes, etc., as the case may be, of the polynucleotide, e.g., a fragment of the ligands, substrates, receptors, enzymes, etc.; or small molecules which bind to the polynucleotide of the present invention but do not elicit a response, so that the activity of the polynucleotide is prevented.

Certain of the polynucleotides of the invention are biomimetics, functional mimetics of the natural fucose kinase polynucleotide. These functional mimetics may be used for, among other things, antagonizing the activity of fucose kinase polynucleotide. Functional mimetics of the polynucleotides of the invention include but are not limited to truncated polynucleotides. For example, preferred functional mimetics include, a polynucleotide comprising the polynucleotide sequence set forth in SEQ ID NO:1 lacking 5, 10, 20, 30, 40, 50, 60, 70 or 80 5' and/or 3' nucleotide residues, including fusion promoters comprising one or more of these truncated sequences. Polynucleotides of these functional mimetics may be used to drive the expression of expression cassettes and marker genes. It is preferred that these cassettes comprise 5' and 3' restriction sites to allow for a convenient means to ligate the cassettes together when desired. It is further preferred that these cassettes comprise gene expression signals known in the art or described elsewhere herein.

Thus, in another aspect, the present invention relates to a screening kit for identifying agonists, antagonists, ligands, receptors, substrates, enzymes, etc. for a polynucleotide of the present invention; or compounds which decrease or enhance the production of such polynucleotides , which comprises: (a) a polynucleotide of the present invention; or (b) a recombinant cell expressing a polynucleotide of the present invention; which polynucleotide is preferably that of SEQ ID NO:1.

It will be appreciated that in any such kit, (a) or (b) may comprise a substantial component.

It will be readily appreciated by the skilled artisan that a polynucleotide of the present invention may also be used in a method for the structure-based design of an agonist, antagonist or inhibitor of the polynucleotide, by: (a) determining in the first instance the three-dimensional structure of the polynucleotide, or complexes thereof, (b) deducing the three-dimensional structure for the likely reactive site(s), binding site(s) or motif(s) of an agonist, antagonist or inhibitor; (c) synthesizing candidate compounds that are predicted to bind to or react with the deduced binding site(s), reactive site(s), and/or motif(s); and (d) testing whether the candidate compounds are indeed agonists, antagonists or inhibitors.

It will be further appreciated that this will normally be an iterative process, and this iterative process may be performed using automated and computer-controlled steps.

In a further aspect, the present invention provides methods of treating abnormal conditions such as, for instance, a Disease, related to either an excess of, an under-expression of, an elevated activity of, or a decreased activity of fucose kinase polynucleotide.

If the expression and/or activity of the polynucleotide is in excess, several approaches are available. One approach comprises administering to an individual in need thereof an inhibitor compound (antagonist) as herein described, optionally in combination with a pharmaceutically acceptable carrier, in an amount effective to inhibit the function and/or expression of the polynucleotide, such as, for example, by blocking the binding of ligands, substrates, receptors, enzymes, etc., or by inhibiting a second signal, and thereby alleviating the abnormal condition. In still another approach, promoter activity can be inhibited using expression blocking techniques. This blocking is preferably targeted against transcription. An examples of a known technique of this sort involve the use of antisense sequences, either internally generated or separately administered (see, for example, O'Connor, *J Neurochem* (1991) 56:560 in Oligodeoxynucleotides as Antisense Inhibitors of Gene Expression, CRC Press, Boca Raton, Fla. (1988)). Alternatively, oligonucleotides which form triple helices with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo. Thus promoter polynucleotides of the invention are useful for ascertaining the functionality or essentiality of the target gene (gene-of-interest) in a cell through expression blocking techniques. A method comprises "knocking-out" the transcription or expression of gene-of-interest by expressing an anti-sense sequence to the gene-of-interest under the transcriptional control of the promoter polynucleotides of the invention, particularly those contained in SEQ ID NO:1. In another embodiment, the method comprises, in a cell, (a) disabling ("knocking-out") the gene-of-interest; (b) reintroducing, at the target gene locus, the gene-of-interest now under the operational control of the inducible promoter polynucleotides of the invention (particularly those contained in SEQ ID NO:1); and (c) adding the inducer thereby providing information to the essentiality or functionality of the gene of interest.

*Helicobacter pylori* (herein "*H. pylori*") bacteria infect the stomachs of over one-third of the world's population causing stomach cancer, ulcers, and gastritis (International Agency for Research on Cancer (1994) *Schistosomes, Liver Flukes and Helicobacter Pylori* (International Agency for Research on Cancer, Lyon, France, http://www.uicc.ch/ecp2904.htm). Moreover, the International Agency for Research on Cancer recently recognized a cause-and-effect relationship between *H. pylori* and gastric adenocarcinoma, classifying the bacterium as a Group I (definite) carcinogen. Preferred antimicrobial compounds of the invention (agonists and antagonists of fucose kinase polynucleotides) found using screens provided by the invention, or known in the art, particularly narrow-spectrum antibiotics, should be useful in the treatment of *H. pylori* infection. Such treatment should decrease the advent of *H. pylori*-induced cancers, such as gastrointestinal carcinoma. Such treatment should also prevent, inhibit and/or cure gastric ulcers and gastritis.

GLOSSARY

The following definitions are provided to facilitate understanding of certain terms used frequently herein.

"Bodily material(s) means any material derived from an individual or from an organism infecting, infesting or inhabiting an individual, including but not limited to, cells; tissues and waste, such as, bone, blood, serum, cerebrospinal fluid, semen, saliva, muscle, cartilage, organ tissue, skin, urine, stool or autopsy materials.

"Disease(s)" means any disease caused by or related to infection by a bacteria, including, for example, otitis media, conjunctivitis, pneumonia, bacteremia, meningitis, sinusitis, pleural empyema and endocarditis, and most particularly meningitis, such as for example infection of cerebrospinal fluid.

"Host cell(s)" is a cell which has been transformed or transfected, or is capable of transformation or transfection by an exogenous polynucleotide sequence.

"Identity," as known in the art, is a relationship between two or more polypeptide sequences or two or more polynucleotide sequences, as the case may be, as determined by comparing the sequences. In the art, "identity," also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.,* 48: 1073 (1988). Methods to determine identity, are designed to give the largest match between the sequences tested. Moreover, methods to determine identity, are codified in publicly available computer programs. Computer program methods to determine identity, between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, MD 20894; Altschul, S., et al., *J. Mol. Biol.* 215: 403–410 (1990). The well known Smith Waterman algorithm may also be used to determine identity.

Parameters for polypeptide sequence comparison include the following: Algorithm: Needleman and Wunsch, J. Mol Biol. 48: 443–453 (1970)

Comparison matrix: BLOSSUM62 from Hentikoff and Hentikoff, Proc. Natl. Acad. Sci. USA. 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm: Needleman and Wunsch, J. Mol Biol. 48: 443–453 (1970)

Comparison matrix: matches=+10, mismatch=0

Gap Penalty: 50

Gap Length Penalty: 3

Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity, to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity, divided by 100 and then subtracting that product from said total number of nucleotides in SEQ ID NO:1, or:

$$n_n \leq x_n - (x_n \cdot y),$$

wherein $n_n$ is the number of nucleotide alterations, $X_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $X_n$ and y is rounded down to the nearest integer prior to subtracting it from $x_n$.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity, is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \cdot y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

"Individual(s)" means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Organism(s)" means a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillis, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia and Mycoplasma, and further including, but not limited to, a member of the species or group, Group A Streptococcus, Group B Streptococcus, Group C Streptococcus, Group D Streptococcus, Group G Streptococcus, *Streptococcus pneumoniae, Streptococcus pyogenes, Streptococcus agalactiae, Streptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyi*, Bordetella, *Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii* and *Chlamydia trachomitis*, (ii) an archaeon, including but not limited to Archaebacter, and (iii) a unicellular or filamentous eukaryote, including but not limited to, a protozoan, a fungus, a member of the genus Saccharomyces, Kluveromyces, or Candida, and a member of the species *Saccharomyces ceriviseae, Kluveromyces lactis*, or *Candida albicans.*

"Polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES,* 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS*, B. C. Johnson, Ed., Academic Press, New York (1983); Seifter et al., *Meth. Enzymol.* 182:626–646 (1990) and Rattan et al., *Protein Synthesis: Posttranslational Modifications and Aging*, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Recombinant expression system(s)" and "recombinant replication system(s)" refers to expression systems or portions thereof or polynucleotides of the invention introduced or transformed into a host cell or host cell lysate for the production of the polynucleotides and polypeptides of the invention.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes include variants of each of the polypeptides of the invention, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gin; and among the basic residues Lys and Arg; or aromatic residues Phe and Tyr. Particularly preferred are variants in which several, 5–10, 1–5, 1–3, 1–2 or 1 amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

The examples below are carried out using standard techniques, which are well known and routine to those of skill in the art, except where otherwise described in detail. The examples are illustrative, but do not limit the invention.

Example 1

Strain selection, Library Production and Sequencing

The polynucleotide having a DNA sequence given in Table 1 [SEQ ID NO:1] was obtained from a library of clones of chromosomal DNA of *Streptococcus pneumoniae* in *E. coli*. The sequencing data from two or more clones containing overlapping *Streptococcus pneumoniae* DNAs was used to construct the contiguous DNA sequence in SEQ ID NO:1. Libraries may be prepared by routine methods, for example: Methods 1 and 2 below.

Total cellular DNA is isolated from *Streptococcus pneumoniae* 0100993 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, Alul, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2

Gene Essentiality Assay

A promoter replacement cassette is generated using PCR technology. The cassette consists of a pair of 500 bp chromosomal DNA fragments flanking an erythromycin resistance gene divergently transcribed with respect to the inducible/repressible promoter. The chromosomal DNA sequences are the 500 bp preceding and following the promoter region of the gene whose essentiality is going to be tested.

The promoter replacement cassette is introduced into *S. pneumoniae* R6 by transformation. Competent cells are prepared according to published protocols. DNA is introduced into the cells by incubation of $\mu$g quantities of promoter replacement cassette with $10^6$ cells at 30° C. for 30 minutes. The cells are transferred to 37° C. for 90 minutes to allow expression of the erythromycin resistance gene. Cells are plated in agar containing 1 $\mu$g erythromycin per ml and the appropriate concentration of the inducer molecule. Following incubation at 37° C. for 36 hours, colonies are picked and grown overnight in Todd-Hewitt broth supplemented with 0.5% yeast extract and the appropiate amount of inducer. Gene essentiality is tested by decreasing the amount of inducer and/or increasing the amount of repressor and monitoring cell viability. If the promoter replacement has occurred upstream of an essential gene, viability of the bacteria will be absolutely dependent on the presence of inducer or the absence of repressor.

Example 3

Identification of Promoter Sequences

Blast searches are run using proteins involved in sugar metabolism in *E. coli* and *B. Subtilis* against SmithKline Beecham's proprietory *S. pneumoniae* genome sequence database. This allows the identification of genes belonging to sugar operons. The location of groups of sugar metabolism genes is used to identify intergenic (noncoding) regions which are considered to contain promoters. In addition, putative promoter sequences are identified by homology with a consensus sequence for bacterial promoters. Such a sequence consists of a −10 region (TATAAT), a 17 bp/19 bp spacer and a −35 region (TTGACA). *S. pneumoniae* promoters have sometimes a characteristic extended −10 region (TNTGNTATAAT) [SEQ ID NO:2] and lack a −35 region. In Seq ID $N_o$1 a −10 ($^{142}$TATAAT$^{147}$) and −35 ($^{119}$TTGAAA$^{124}$) regions have been identified. This promoter controls the fucose metabolism operon. The first gene of the operon (fucose kinase) encodes fucose kinase.

Example 4

Fucose Kinase Characterization

Identification of the Fucose Kinase Gene Transcription Initiation Site a) Preparation of Pre-inoculum and Growth Conditions

*S. pneumoniae* R6 is grown statically at 37° C. in the semi-defined AGCH media (Lacks S. (1968). Genetics 60: 4685–706.), supplemented with 0.2% yeast extract (YE) and different test sugars added as the sole sugar source. In a preliminary experiment, *S. pneumoniae* was shown to grow to an $OD_{650}$ of 0.6 at approximately the same growth rate, when sucrose, glucose, trehalose or lactose were added to the medium at the point of inoculation as the sugar source at 1% (w/v) final concentration. Where *S. pneumoniae* was unable to utilize a sugar as the single carbon source (fucose and galactose), or showed a significantly reduced growth rate (raffinose), glucose was supplemented to the media at a concentration of 0.2% (w/v) to maintain growth.

The sugar growth conditions tested are 1% glucose, 1% sucrose, 1% lactose, 1% trehalose, 1% fructose, 1% mannose, 0.2% glucose, 0.2% glucose+1% fucose, 0.2% glucose+1% galactose, 0.2% glucose+0.5% raffinose and 1% raffinose.

To adapt *S. pneumoniae* to growth in the test sugar(s), 100 μl of a glycerol stock of *S. pneumoniae* R6 is diluted in 4 ml of AGCH +YE media supplemented with the test sugar(s) and grown to exponential phase until $OD_{650}$ reached 0.29–0.31. Cultures (0.1 ml) are rediluted in 4 ml fresh AGCH +YE containing the same sugar(s) and re-incubated at 37° C. to exponential phase. This is repeated for a third time. Glycerol is added to 10% (v/v) final concentration, and cells are frozen in dry ice/ethanol bath and stored at −70° C. as stocks of "synchronised" *S. pneumoniae* cells adapted to different sugar(s) as carbon source(s).

To isolate RNA, *S. pneumoniae* cells are grown under appropriate sugar conditions to an $OD_{650}$ of 0.6.

b) Isolation of *Streptococcus pneumoniae* R6 RNA.

RNA is extracted using the FastRNA Kit (Biol101) according to the manufacturers instuctions with slight modifications. Briefly, 5 ml of *S. pneumoniae* cells are centrifuged at 6000 rpm and 4° C., the supernatanrt is removed and the pellet is resuspended in 200 μl of AGCH and added to a FastPrep tube containing lysing matrix and 1 ml of extraction reagents (FastRNA). The tubes are shaken in a reciprocating shaker (FastPrep FP120, BIO101) at 6000 rpm for 45 sec. The crude RNA preparation is extracted with chloroform/isoamyl alcohol (24:1), and precipitated with DEPC-treated/Isopropanol Precipitation Solution (BIO101). RNA preparations are stored in this isopropanol solution at −80° C. if necessary. The RNA is pelleted (12,000 g for 10 min.), washed with 75% ethanol (v/v in DEPC-treated water), air-dried for 5–10 min, and resuspended in 0.1 ml of DEPC-treated water, followed by 5–10 minutes at 55° C. Finally, after at least 1 minute on ice, 200 units of Rnasin (Promega) are added.

RNA preparations are stored at −80° C. for up to one month. For longer term storage the RNA precipitate can be stored at the wash stage of the protocol in 75% ethanol for at least one year at −20° C.

Quality of the RNA isolated is assessed by running samples on 1% agarose gels. 1×TBE gels stained with ethidium bromide are used to visualise total RNA yields.

c) The removal of DNA from *Streptococcus pneumoniae*-derived RNA

DNA is removed from 50 microgram samples of RNA by a 30 minute treatment at 37° C. with 20 units of RNAase-free DNAaseI (GenHunter) in the buffer supplied in a final volume of 57 microliters.

The DNAase is inactivated and removed by treatment with TRIzol LS Reagent (Gibco BRL, Life Technologies) according to the manufacturers protocol.

DNAase treated RNA is resuspended in 100 microlitres of DEPC treated water with the addition of Rnasin as described before.

d) Primer extension analysis

15 μg of DNAse-treated RNA is denatured together with 5 pmol of 6-FAM-5' fluorescently tagged primer (5' CAAGAATTTTAGCTAGTAGAAAGTCAATATC3') [SEQ ID NO:3] (PE Applied Biosystems), corresponding to the 5' end of the fucose kinase gene, in 10 μl final volume at 70° C. for 10 min. The mixture is allowed to cool down to 55° C. over a 30 min period and 10 μl of cDNA synthesis reagents (Thermoscript RT-PCR System, Gibco BRL) are added. cDNA synthesis is performed at 55° C. for 60 min. After denaturation of the reverse transcriptase at 85° C. for 5 min, the RNA is degraded by a RNAse treatment at 37° C. for 20 min with 2 units of RNAse H and 2196 units of RNAse T.

Primers are eliminated from the cDNA samples using a QIAquick PCR Purification Kit (QIAGEN) according to the manufacturers instructions but eluting the cDNA in 20 μl of DEPC-treated water in the final step. The cDNA is precipitated with 2.5 volumes 100%EtOH, 1/10 vol. 3M NaOAc and 10 mg/ml yeast tRNA overnight at −20 ° C. and recovered by centrifugation at 15,000 g for 10 minutes. Air dried pellets are resuspended in 2 μl formamide, 0.5 μl Blue Dextran loading dye and 0.5 μl Genescan 500XL Rox Size Standard (PE Applied Biosystems). Samples are loaded onto 34 well, 48 cm Sequencing gel (BMA) and separated using Perkin Elmer's ABI 377XL Sequencer Electrophoresis set. Data is examined using Perkin Elmer's ABI Prism Genescan Analysis 2.1 Software.

The transcription initiation site for the fucose kinase gene was the A located at position 155 from Seq ID No1, 8 bp downstream of the predicted −10 region confirming the existance of the promoter.

Example 5

Expression of the Fucose Kinase Promoter is Regulated by Sugars

Growth Conditions and Preparation of RNA are Identical to that Especified in Example 4 a) The Preparation of cDNA from RNA Samples 5 microgram samples of DNAase-treated RNA are reverse transcribed using a SuperScript Preamplification System for First Strand cDNA Synthesis kit (Gibco BRL, Life Technologies) according to the manufacturers instructions. 250 nanogram of random hexamers is used to prime each reaction. Controls without the addition of SuperScriptII reverse transcriptase (RT) are also run. Both +/−RT samples are treated with RnaseH. cDNA samples were stored at −20° C.

b) The Use of PCR and SybrGreen Dye Accumulation to Quantitate Bacterial mRNA

Specific sequence quantification occurs by amplification of target sequences in the PE Applied Biosystems 7700 Sequence Detection System with template specific primers and in the presence of Sybr Green dye. Amplification with annealing temperatures that only allow specific product formation is monitored by measuring the signal generated by accumulation of Sybr Green dye with an attached CCD camera. Standardization to chromosomal DNA allows correlation between signal generated and product accumulated. Relative quantitation is normalized to a housekeeping gene and a calibrator sample (uninduced control).

PCR reactions are set up using the PE Applied Biosystem SybrGreen PCR Core Reagent Kit according to the instructions supplied such that each reaction contains 5 microliters 10×SybrGreen buffer, 7 microliters 25 mM $MgCl_2$, 5 microliters 300 nM forward primer, 5 microliters reverse primer, 1 microliter each 10 mM dATP, 10 mM dCTP, 10 mM dGTP and 20 mM dUTP, 13.25 microliters distilled water, 0.5 microliters AmpErase UNG, and 0.25 microliters AmpliTaq DNA polymerase to give a total volume of 45 microliters.

Amplification proceeds under the following thermal cycling conditions: 50° C. hold for 2 minutes, 95° C. hold for 10 minutes, 40 cycles of 95° C. for 15 seconds and 60° C. for 1 minute, followed by a 25° C. hold until sample is retrieved. Detection occurs real-time. Data is collected at the end of the reaction.

RT/PCR controls may include no reverse transcriptase reactions to verify the absence of contaminating genomic DNA.

Primers used for Example 5 are as follows:

| | |
|---|---|
| ATCCGCTTGGCTAATACTA [SEQ ID NO:4] | fwd primer |
| ATCGCCTAAACCATACTCC [SEQ ID NO:5] | rev primer |

Sybr Green quantitation of accumulating PCR product and the uses of such a technique have reported: (Morrison T. B, Weis J. J and Wittwer C. T. 1998. Quantification of low-copy transcripts by continuous SYBR green I monitoring during amplification. BioTechniques 24:954–962. Wittwer C. T., Herrmann M. G., Moss A. A., Rasmussen R. P. 1997. Continuous fluorescence monitoring of rapid cycle DNA amplification. Biotechniques 22:130–131, 134–1388).

Such an experiment showed that expression of the fucose kinase promoter is induced by 1% fucose+0.2% glucose and is repressed by 0.2% glucose.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

What is claimed is:

1. An isolated polynucleotide comprising a nucleic acid sequence, wherein the nucleic acid sequence comprises SEQ ID NO:1 and wherein the nucleic acid sequence is not genomic DNA.

2. A vector comprising the isolated polynucleotide of claim 1.

3. An isolated host cell comprising the vector of claim 2.

* * * * *